United States Patent

Pomatto

[11] Patent Number: 5,951,503
[45] Date of Patent: Sep. 14, 1999

[54] CRANIAL ORTHOSIS BAND

[76] Inventor: Jeanne K. Pomatto, 7665 E. Larkspur, Scottsdale, Ariz. 85260

[21] Appl. No.: 08/720,529

[22] Filed: Sep. 30, 1996

[51] Int. Cl.[6] ....................................................... A61F 5/00
[52] U.S. Cl. .............................................................. 602/17
[58] Field of Search .................................. 602/5, 14, 17, 602/18; 128/857, 889; 2/425; D29/102

[56] References Cited

U.S. PATENT DOCUMENTS

| | | | |
|---|---|---|---|
| 3,503,392 | 3/1970 | Beeman | 128/889 |
| 4,776,324 | 10/1988 | Clarren | 602/17 |
| 5,094,229 | 3/1992 | Pomatto et al. | 602/17 |
| 5,123,408 | 6/1992 | Gaines | 602/17 |
| 5,201,702 | 4/1993 | Mars | 602/17 |
| 5,205,813 | 4/1993 | Schmidt | 602/17 |
| 5,308,312 | 5/1994 | Pomatto et al. | 602/17 |
| 5,549,678 | 8/1996 | Prostkoff | 602/14 X |

*Primary Examiner*—Linda C.M. Dvorak
*Attorney, Agent, or Firm*—Donald J. Lenkszus; Bryan Cave, LLP

[57] ABSTRACT

A cranial orthosis band is shaped to extend across the top of the head with depending regions closely confining the temporal bone regions and the mastoid process regions of the cranium. The orthosis includes a rear region which encloses the occipital bone region of the cranium so that flattening of the rear of the head can be treated or prevented. The orthosis is self-suspending. The rear portion of the orthosis imparts ear-to-ear rigidity to the device.

12 Claims, 5 Drawing Sheets

CRANIAL ORTHOSIS BAND

TECHNICAL FIELD

This invention pertains to a cranial orthosis band device, in general, and to a cranial orthosis band which may be used for correcting and or preventing flattening of the rear of the head.

BACKGROUND OF THE INVENTION

Approximately one of every three hundred children may be afflicted with a misshapen head or cranial abnormality. Various courses of treatments have been developed in the past. Where cranial sutures have closed, surgery may be resorted to correct abnormalities of the cranium. If treatment is undertaken before the patient's cranial sutures have closed, i.e., at an early age, preferably when the patient is less than six months old, the less invasive and more desirable methodology of cranial remodeling for correcting these problems may be utilized. The use of a cranial remodeling orthosis has proven to be highly effective and successful for treatment of a variety of cranial abnormalities.

In U.S. Pat. No. 5,094,229 granted Mar. 10, 1992 for "CRANIAL REMODELING ORTHOSIS", and to which the present Applicant is a coinventor, different approaches to cranial remodeling are described and an improved cranial remodeling orthosis band for correcting plagiocephaly is disclosed.

A particular form of abnormality can be corrected with a somewhat different orthosis design and treatment methodology and is described in U.S. Pat. No. 5,308,312 granted May 3, 1994 for "CRANIAL REMODELING ORTHOSIS" and to which the present Applicant is also a coinventor. This abnormality is known as brachycephalic cranial head shape abnormality. The brachycephalic head shape is characterized by occipital flattening of the cranium. The resultant biparietal breadth and/or height abnormalities are usually accompanied by bi-temporal and frontal breadth abnormalities. The supernormal brachycephalic head shape is one in which the maximum cranial breadth is disproportionately large in relation to the maximum cranial length.

An orthosis band of the type described in the '312 patent corrects brachycephaly by constraining growth across the breadth and height of the cranium while encouraging an increase in the maximum cranial length. The orthosis band is configured to extend across the top of a head with side or depending regions closely confining the temporal bone regions and the mastoid process regions of the cranium. The orthosis is self-suspending, i.e., it does not require a chin strap of other means to cause it to remain in position. A reinforcing band is integrally formed into the top of the band to provide ear to ear rigidity.

The incidence of cranial abnormalities in infants is increasing. In particular, it is believed that approximately one in two hundred infants now exhibits cranial abnormalities. The increase may be a result of the methodology which has been recommended for reducing the likelihood of Sudden Infant Death Syndrome (SIDS). That methodology recommends having infants sleep on their backs at all times. The result of having the infant sleep in the same position causes a flattening of the back of the head. This abnormality may occur by itself or in combination with other abnormalities. It is therefore desirable to provide a means for correcting this specific abnormality and for providing a means for preventing flattening of the rear of the head while permitting continued use of the SIDS preventive methodology of bedding infants on their backs.

SUMMARY OF THE INVENTION

In accordance with the principles of the invention, an improved cranial orthosis device is provided which may be used to correct for flattening of the rear of the head. Further in accordance with the invention, an orthosis device is provided which will allow an infant to be put to bed on his/her back and protect against flattening of the cranium.

A cranial orthosis device in accordance with the invention is self-suspending and further includes apertures through which the condition of the cranium may be observed and also which may permit ventilation.

A cranial orthosis device in accordance with the invention extends across the top of the patient's head and includes depending regions which closely confine the temporal bone regions and the mastoid process regions of the cranium. A rear region of the orthosis encloses the occipital bone region of the cranium. The rear region conforms to the desired shape of the occipital region. Where the occipital region has been flattened, wearing of the orthosis is a treatment which will remodel the shape of the occipital region to the desired shape.

Where the occipital region has not deformed, wearing the orthosis is a preventive measure whereby flattening of the occipital region is prevented. The rear region imparts ear-to-ear rigidity to the orthosis to improve the self-suspending capability of the orthosis.

The orthosis devices of the invention are preferably custom fitted to each patient.

In accordance with the invention, flattening of the occipital region of the cranium in infants may be prevented by having the infant wear an orthosis device in accordance with the invention each time the infant is put to bed.

BRIEF DESCRIPTION OF THE DRAWINGS

The invention will be better understood from a reading of the following detailed description in conjunction with the drawings in which.

DETAILED DESCRIPTION

Figure 1:
FIG. 1 is a front view of an infant's head, illustrating the abnormality known as brachycephaly in combination with a flattening of the posterior of the cranium.
Figure 2:
FIG. 2 is a side view of the infant of FIG. 1.
Figure 3:
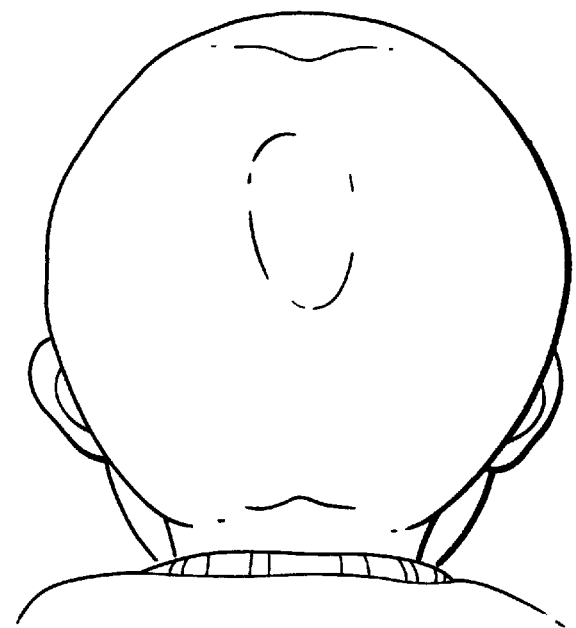
FIG. 3 is a rear view of the infant of FIG. 1.
Figure 4:
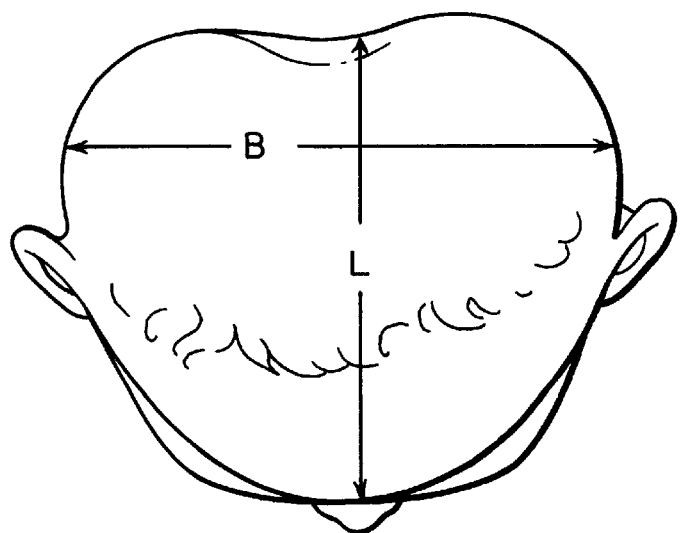
FIG. 4 is a top view of the infant of FIG. 1.

The infant shown in FIGS. 1 through 4 illustrate the cranial abnormality known as "brachycephaly". This abnormality is one of several different classifiably different abnormalities to which the present invention may provide an effective treatment. The abnormality is manifested as a cranial condition in which the breadth "B" of the cranium is disproportionately large in relation to the length "L" of the cranium. The illustration of the infant also shows the infant having a flattening of the rear of the head. This flattening may occur as a result of the routine placing of the infant on his/her back to avoid Sudden Infant Death Syndrome.

Figure 5:
FIG. 5 is a front view of an orthosis device constructed in accordance with this invention in place on the infant of FIG. 1.
Figure 6:
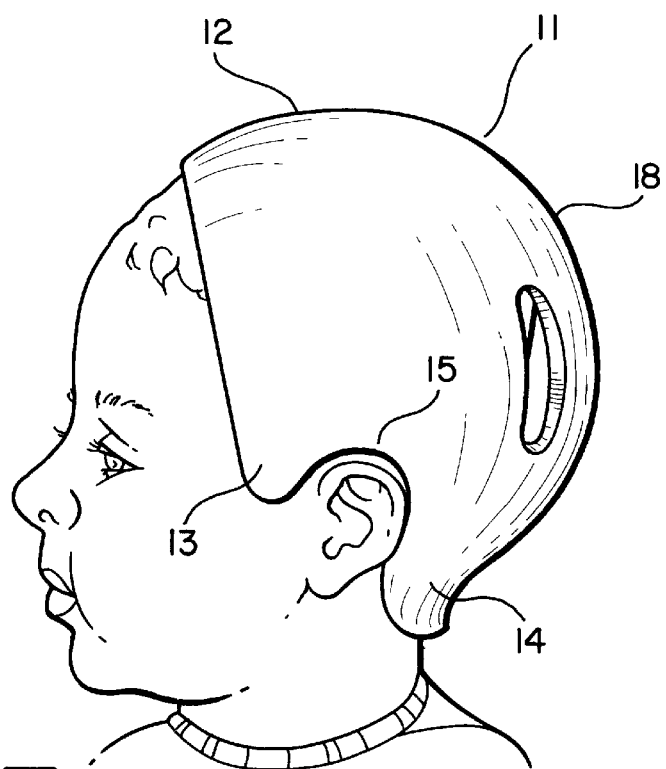
FIG. 6 is a side view of the orthosis device and infant.
Figure 7:
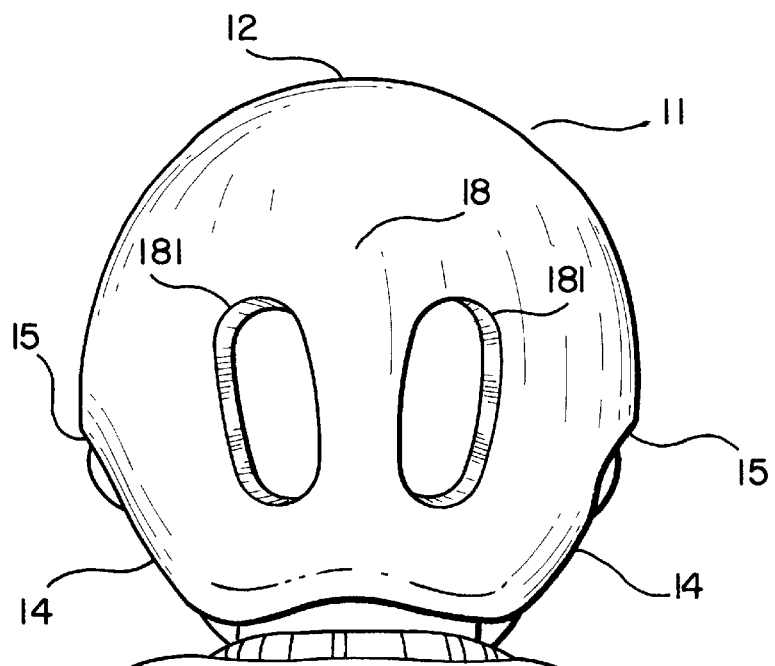
FIG. 7 is a rear view of the orthosis device and infant.
Figure 8:
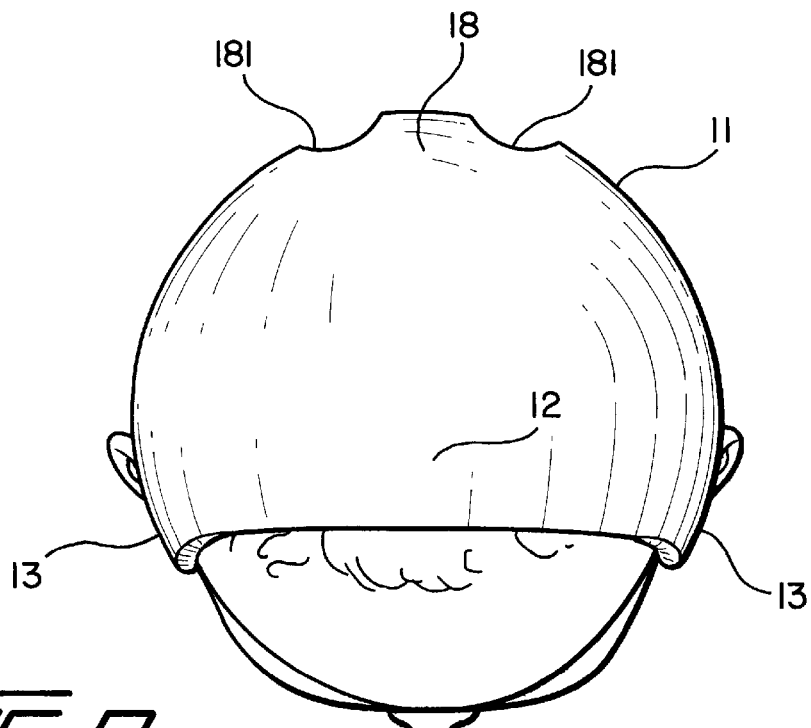
FIG. 8 is a top view of the orthosis device and infant.
Figure 9:
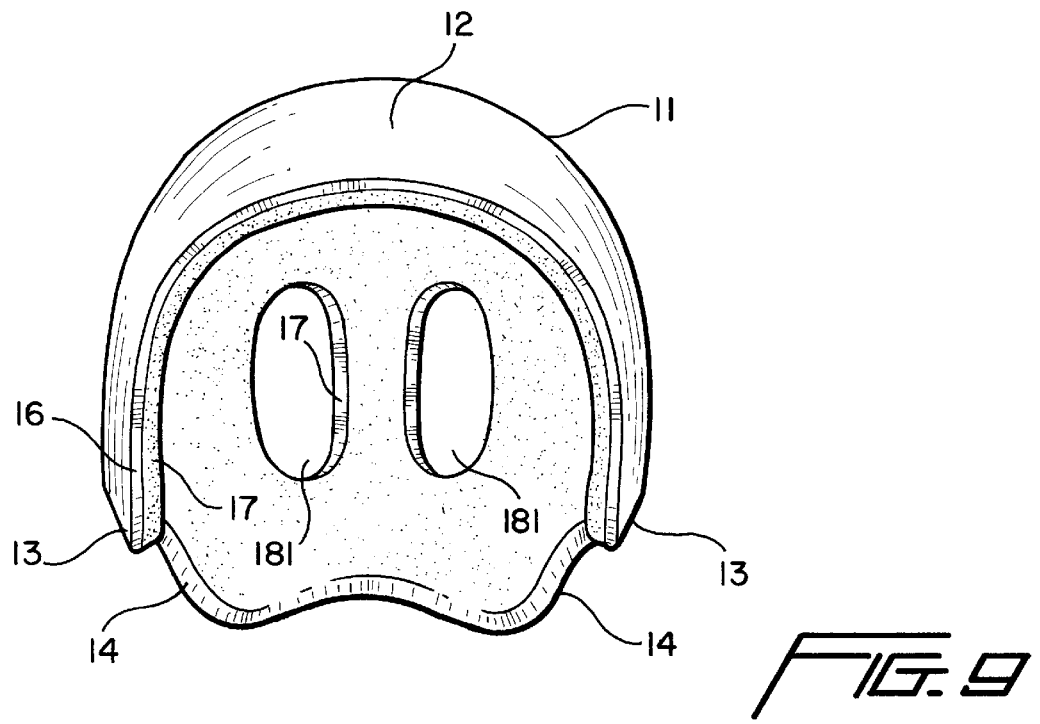
FIG. 9 is a front view of the orthosis of the orthosis device.
Figure 10:
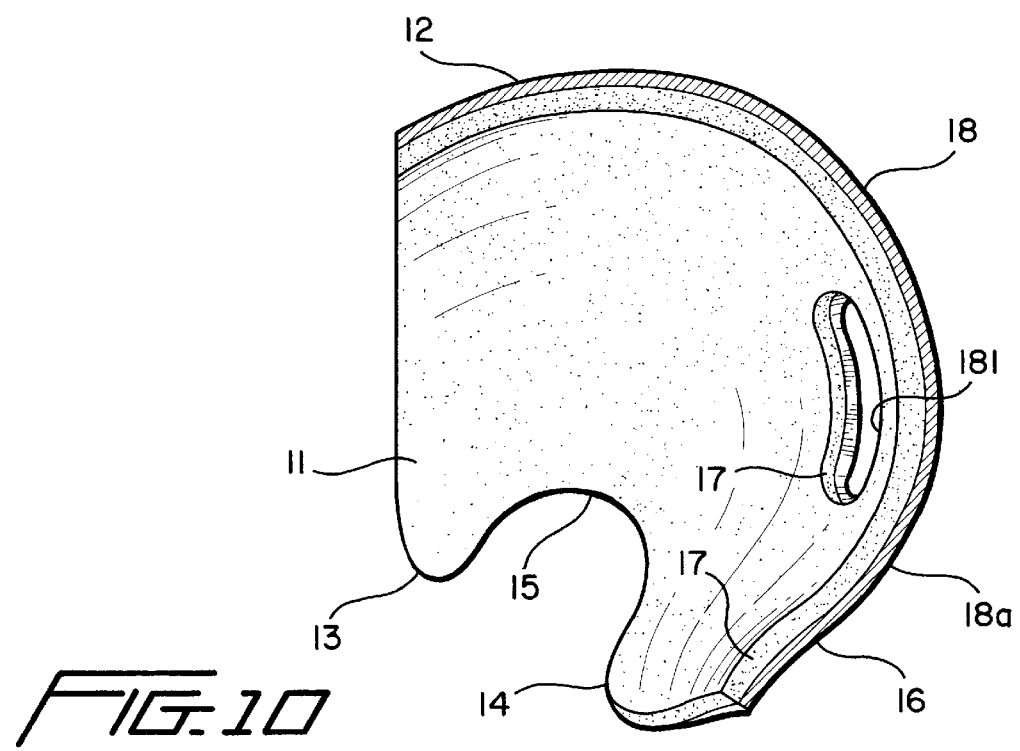
FIG. 10 is a sectional view of the orthosis device taken from line 10—10 in FIG. 8.

A cranial remodeling orthosis band in accordance with the invention is illustrated in FIGS. 5 through 10. The orthosis 11 is employed to remodel the cranium by allowing growth of the cranium length to the configuration shown by the dashed outline while constraining growth of the cranium in breadth.

The orthosis band 11 is formed to allow for the growth of the cranium into a natural symmetrical generally rounded shape.

As shown in FIGS. 5 through 10, the orthosis band 11 includes a central or upper region 12 which is shaped to extend over the top and closely conform to the configuration of the top of the cranium. For most patients, this upper region 12 of the orthosis will cover an anterior region of the parietal bone and possibly a posterior region of the frontal bone.

Integrally associated with the central region 12 of the orthosis are depending side regions 13 and 14 on each side of the orthosis. Depending side regions 13 are shaped to closely confine temporal bone regions of the cranium adjacent and forward of the ears of the subject. Depending side regions 14 are shaped to closely confine mastoid process regions of the cranium to the rear and beneath the ears of the subject. Cut out regions 15 between depending regions 13 and 14 uncover the ears of the patient.

The orthosis device 11 further includes an integrally formed posterior region 18 which encloses the occipital bone region. In the illustrative orthosis device shown, the region 18 is shaped to allow for growth of the infant's head into a normal symmetrically ovoid shape as shown by the dashed lines in FIG. 2. It should also be apparent that the region 18 may be shaped to conform to the infant's actual head shape in the occipital bone region for those applications in which the orthosis is to be used to maintain the infant's head shape, i.e., no correction of the occipital bone region is necessary.

The orthosis device 11 is configured to be self-suspending, i.e., remain in stabilized position on the cranium of the subject without the aid of a chin strap. Others have attempted to use helmet-type orthosis devices as cranial remodeling devices. However, helmet type devices typically extend over the forehead of the patient. Helmet type devices are not self suspending and therefore require the use of a chin strap to retain them in position. The use of a chin strap is undesirable for several reasons, including the reason that it can result in unintended deformity of the infant's jaw bone or other facial bones. Another reason is that the strap may cause choking.

Orthosis band 11 is made self-suspending by forming the orthosis regions 13 and 14 such that the temporal bone and mastoid process regions of the cranium are closely confined. The regions of contact formed by orthosis regions 13 and 14 fall within planes of the cranium which have circumferences which are less than the maximum occipitofrontal circumference of the subject's cranium. This is most apparent from the top view of the orthosis shown in FIGS. 5 and 7 where the side regions 13 and 14 respectively are shown.

Likewise, the rear region 18 includes lower portions 18a which are also of a circumference which is less than maximum circumference of the occipital bone region. This is most apparent in FIG. 10 where the lower portion 18a of the region 18 is shown. Posterior region 18 contributes to the self-suspending feature of the orthosis 11 by its shape as well as providing ear to ear rigidity to the orthosis. In my prior orthosis, ear to ear rigidity was increased in the orthosis band by means of an integrally formed top reinforcing band.

The orthosis band 11 is formed from material which has inherent resiliency. This configuration of the orthosis band 11 and the inherent resiliency cooperate to draw the orthosis band 11 down on the head such that the central region 12 contacts the top of the patient's head and holds orthosis band 11 in place.

An additional feature of the orthosis is shown in FIGS. 7 through 10. The orthosis band includes apertures 181 disposed in the region 18. Each of these apertures 181 is of oblong shape. The three apertures shown are positioned so that visual inspection of the rear of the patient's head can occur with the orthosis in place. In addition, the apertures 181 provide for ventilation. It should be apparent that a combination of different shaped apertures may also be utilized with some being large enough and oriented so that visual observation of the back of the infant's head may occur and others provided primarily for ventilation. In the illustrative orthosis band, two apertures 181 are disposed and of such size that both observation and ventilation occurs with each aperture.

Orthosis band 11 is constructed with an outer layer 16 of plastic material and an inner liner 17 of compressible foam material. Outer layer 16 is formed of co-polymer polypropylene material approximately 3/16" (4.76 mm) thick. This material is light in weight, possesses considerable strength, is resilient, and possesses shape memory. In the illustrative orthosis band 11, liner 17 is medium density sheet polyurethane foam having a thickness of approximately 3/8" (10 mm).

The region 18 of the orthosis band 11 encases the occipital bone region as well as the posterior of the parietal bone region of the head. The inherent stiffness and resiliency of the outer layer 16 of copolymer polypropylene combined with its shape memory properties is sufficient to hold the orthosis in place. The stiffness and resiliency of polypropylene is also sufficient to effectively restrain growth across the breadth and height of the cranium while retaining the orthosis band 11 in position on the patient's head even when the patient is placed on his/her back. For those applications of the orthosis where cranial remodeling is not the objective, but rather, the objective is to prevent inducement of deformity, the polypropylene material is sufficiently stiff to support the infant's head. By constructing the orthosis 11 with these materials, the orthosis is made lightweight. For the comfort of the patient, it is desirable to keep the weight of the orthosis as low as possible.

Due to the inherent resiliency of the material from which the orthosis is constructed, the orthosis band 11 has some flexibility to permit the opposite sides of the orthosis 11 to be spread apart to put the orthosis on and remove the orthosis from the patient's head.

Although the orthosis band 11 described above is shaped to provide for cranial remodeling, the orthosis band 11 may likewise be formed to prevent the incidence of cranial abnormality from the SIDS methodology as described above. When used for preventive care, the orthosis may be removed when the infant is not asleep. Thus as a preventive device, the orthosis would be placed on the infant's head each time the infant is to be put to bed or perhaps left unattended. When the infant is awake, the orthosis may be removed.

The orthosis band 11 shown in the drawings is custom manufactured to fit the individual patient.

In one method for fabricating the orthosis band, a negative mold of the patient's head is formed. From the negative mold of the head, a positive model of the head is cast. For orthosis bands which are being used only to prevent the occurrence of abnormality rather than for remodeling, the orthosis band may be fabricated directly from the positive model. In those applications of the orthosis band intended to correct abnormalities, the positive model is shaped to account for the remodeling which is required to correct abnormalities as well as the patient's cranial growth. The resultant positive model is then employed to shape an orthosis band 11.

To fabricate the orthosis band, liner material 17 is vacuum formed over the model. The outer layer material 16 is then vacuum formed over the positive model. The model is removed from this structure, trim lines are applied, and the structure is trimmed in accordance with the trim lines to the desired configuration illustrated in the drawing and described above.

What is claimed is:

1. A cranial orthosis device comprising:
   a resilient band adapted to conform to a substantially normally shaped cranium and extend across the parietal bone region of the cranium:
   said band having depending regions shaped to closely confine the temporal bone regions and the mastoid process regions of the cranium with relief areas there between to expose the ears when the orthosis is worn by a patient, said depending regions of the orthosis being adapted to provide regions of contact which fall within planes of the cranium which have circumferences which are less than the maximum occipitofrontal circumference of the cranium whereby the orthosis is held in place on the cranium when in use; and
   a rear depending region shaped and configured to cover the occipital region of the cranium to thereby prevent flattening of the occipital bone region of the cranium.

2. An orthosis in accordance with claim 1 comprising:
   an outer layer of thermoformed plastic material and an inner liner of cushioning material.

3. An orthosis in accordance with claim 1, wherein:
   said rear depending region is in the shape of a desired shape of the occipital region of the cranium of a patient.

4. An orthosis in accordance with claim 3, wherein:
   said orthosis is custom fit to the head of a patient such that wearing said orthosis remodels the shape of said patient's cranium.

5. An orthosis in accordance with claim 1, wherein:
   said orthosis includes at least one aperture disposed to permit visual observation of the occipital region of the cranium of said patient.

6. An orthosis device in accordance with claim 1, wherein:
   said orthosis includes a plurality of apertures.

7. An orthosis device in accordance with claim 6, wherein:
   at least certain of said apertures are disposed to permit visual inspection of said patient's cranium while said orthosis is being worn by said patient.

8. An orthosis device in accordance with claim 7, wherein:
   said apertures provide ventilation.

9. A cranial orthosis comprising:
   portions configured to contact a substantially normally shaped cranium of a patient in selected first areas of the cranium of said patient;
   second portions configured to enclose the occipital region of the cranium and to prevent flattening of the occipital bone region of the cranium;
   regions contacting said cranium, said regions falling within planes of said cranium which are less than the maximum occipitofrontal circumference of said cranium, whereby said orthosis is made self-suspending;
   said orthosis being of one piece construction.

10. An orthosis in accordance with claim 9 comprising at least one aperature in said second portions.

11. An orthosis in accordance with claim 9 comprising a resilient plastic material.

12. An orthosis in accordance with claim 9 comprising relief areas for the ears of said patient.

* * * * *